United States Patent [19]
Frederiksen

[11] Patent Number: 5,626,904
[45] Date of Patent: May 6, 1997

[54] SALT PRODUCT AND A METHOD FOR THE PREPARATION THEREOF

[75] Inventor: Wilmar F. Frederiksen, Vedbæk, Denmark

[73] Assignee: Hitavejta Sudurnesja, Njardvik, Iceland

[21] Appl. No.: 295,800

[22] PCT Filed: Mar. 18, 1993

[86] PCT No.: PCT/DK93/00100

§ 371 Date: Sep. 16, 1994

§ 102(e) Date: Sep. 16, 1994

[87] PCT Pub. No.: WO93/18668

PCT Pub. Date: Sep. 30, 1993

[30] Foreign Application Priority Data

Mar. 19, 1992 [DK] Denmark .................. 0362/92

[51] Int. Cl.[6] .................. A23L 1/237; A01N 59/08; C01D 3/04
[52] U.S. Cl. .................. 426/649; 424/665
[58] Field of Search .................. 426/649; 424/665

[56] References Cited

FOREIGN PATENT DOCUMENTS

| | | |
|---|---|---|
| 150601 | 4/1987 | Denmark . |
| 3008171 | 9/1981 | Germany . |
| 59-198953 | 11/1984 | Japan . |
| WO85/00958 | 3/1985 | WIPO . |
| WO90/00522 | 1/1990 | WIPO . |

*Primary Examiner*—Esther Kepplinger
*Assistant Examiner*—Choon P. Koh
*Attorney, Agent, or Firm*—Oblon, Spivak, McClelland, Maier & Neustadt, P.C.

[57] ABSTRACT

A salt product comprising particles of NaCl, K/Mg-double salts and optionally KCl homogeneously distributed throughout each particle and having a molar ratio of K to $Mg \geq 1$. The product may be obtained from an aqueous salt mixture, preferably a solution containing the desired proportion of salt ions and having a water content of 50 to 90% by weight by subjecting the aqueous salt mixture to instant drying at a temperature of 70° to 200° C. for a period of 1 to 60 seconds to obtain a dry product. The product is usable as a low sodium substitution for common salt in connection with the preparation of food, beverages or pharmaceutical products and/or as a preservative or water binding agent.

13 Claims, 3 Drawing Sheets

SALT PRODUCT AND A METHOD FOR THE PREPARATION THEREOF

TECHNICAL FIELD

The present invention relates to a salt product comprising NaCl, K/Mg-double salt and optionally KCl, wherein the molar ratio of K to Mg is $\geq 1$, a method for the preparation thereof and the use thereof as a substitute for ordinary salt in connection with the preparation of food, beverages or pharmaceutical products and/or as a preservative or water binding agent including use as a table salt.

BACKGROUND ART

Common salt, i.e. sodium chloride, is the additive most frequently used in food and beverage preparation both for household and industrial use. It is necessary to consume a certain amount of sodium ions and chloride ions with the food, but the intake of sodium chloride is usually much larger than the minimum required to maintain the salt balance of the body.

To people suffering from certain diseases, such as increased blood pressure, large amounts of NaCl-intake are considered to be injurious. Furthermore, a large intake of sodium ions can displace the balance between sodium and potassium in the body.

Therefore, in order to control the intake of salt, it has been proposed to use various salt combinations, wherein sodium chloride has been partially replaced by other salts, especially potassium chloride.

Replacement of sodium chloride by other chemical compounds pounds entails several disadvantages, inter alia a taste deterioration due to the fact that only sodium chloride can provide the correct salty taste sensation. It is possible to use additives which conceal or disguise this deviation in taste, but only a few additives are acceptable for use in food products. The more the amount of sodium chloride in the salt product is decreased, the greater is the taste deviation problem.

A further problem is that when various pulverulent compounds are intermixed, the mixture will easily become inhomogeneous, especially if it consists of grains of different sizes and densities, which may result in unexpected and unpleasant taste sensations. The problem is particularly distinct when the salt mixture is to be dispensed from a caster. Storing for long periods of time may cause stratification of the product which increases this problem.

WO 86/05954 (Sundien) describes a mineral salt product containing mineral salts in the same relative proportions as in ocean water, apart from a reduced content of sodium chloride. This product contains trace minerals which are considered important for the human health. However, the product has a relatively high content of hygroscopic and bitter magnesium salts.

DE patent publication No. 3,008,171 (Wixforth) discloses a method for the preparation of a salt product by evaporation of water from the Dead Sea. The intermediate salt product obtained contains the K/Mg-double salt carnallite. This intermediate product is, however, unfit for human consumption without the addition of NaCl. The molar ratio of Mg to K is about 7:1 in the Dead Sea, which means that only 1:7 of the magnesium is present as carnallite nallite in the end product. The remaining magnesium will therefore be present as magnesium chloride and/or magnesium sulphate which both are bitter tasting, hygroscopic and present practical problems by storage and use. Furthermore, the NaCl-containing end product is prepared by mere mixing which does not ensure that a homogenous salt product can be obtained.

WO 85/00958 (Rood et al.) discloses a salt product in the form of a mixture comprising 40 to 50% by weight of sodium chloride, 25 to 35% by weight of potassium chloride, and 15 to 25% by weight of magnesium sulphate and/or magnesium chloride. The mixture consists of separate crystals of the same size which should ensure that the mixture is more homogeneous. Rood et al. alleges that by that method, a salt composition is provided which comprises magnesium and potassium salts, has a low NaCl content and has a better taste and a diminished segregation of the different components, when compared with other known low sodium salt mixtures. Even though there might be some improvement with respect to commonly mixed low sodium containing compositions, the salt of Rood does not provide for a fully satisfactory taste, and it is still very hygroscopic due to the presence of hygroscopic magnesium salts. Hence, there still exists a need for further improvement.

Japanese patent application Kokai 84/198953 (Kobayashi Seiyaku K.K.) discloses a salt composition comprising NaCl and KCl mixed with powdered solidified bittern. The concentration of the bittern is in the range of 1–20% by weight based on the total weight of the product. Several preparation methods, including that of dry mixing of the components, are suggested. By another proposal, NaCl, KCl and bittern are dissolved in fresh water and the solution is condensed by a conventional method. As conventional methods, vacuum condensation, kettle condensation and spray drying are mentioned. In case one of these methods is used, the formation of a double salt cannot be excluded in case of very specific conditions. However, such conditions are not disclosed at all, nor is their any hint to the preference of one of these condensation methods. The importance of the double salts was not at all recognized.

WO 90/00522 (Sundström) discloses a salt product for use in household and within industry having a reduced content of sodium chloride, which product comprises crystals of sodium chloride and/or potassium chloride adhered to the crystals of kainite and/or carnallite. Not only is it very difficult to produce pure K/Mg-double salt, but the process as described will be very unpractical, due to all the specific measures that has to be taken care of in order to obtain a coating which does not come off by handling of the product. Furthermore, the product obtained is not homogeneous throughout the particle, and will, due to the presence of potassium chloride in the coating, provide a metallic-bitter aftertaste.

It is the object of the present invention to provide a mineral salt product having a low content of sodium chloride, and which is not encumbered with the above problems and disadvantages with segregation, bitter taste, and hygroscopicity, as well as a simple and economic method for the preparation of the mineral salt product.

BRIEF DESCRIPTION OF THE INVENTION

The invention relates to a salt product comprising NaCl, K/Mg-double salt and optionally KCl, wherein the molar ratio of K to Mg is $\geq 1$, which salt product is characterised by comprising particles in which NaCl and K/Mg-double salt, such as carnallite and/or kainite, as well as KCl, if present, are homogeneously distributed throughout the particles.

The inventive salt product has a remarkably good taste even when the content of NaCl is relatively low.

According to organoleptic comparison tests, the inventive product is comparable to conventional NaCl and has not the metallic-like taste of KCl and the bitter taste of Mg-salts.

When used in the same amounts as a substitute for NaCl by the preparation of various food products, such as butter and cheese, the inventive product gives no perceptible change of the taste. The technical effects, such as water binding and preservation, are also similar to those obtained using pure NaCl.

Furthermore, the inventive salt product is not hygroscopic and can in most gases be stored and distributed without the addition of anti-caking agents or other additives, which would generally be necessary in case of hygroscopic products.

In order to ensure storage stability, the inventive salt product does preferably not contain any hygroscopic Mg-salts.

This is advantageously ensured by substantially all Mg present being in the form of double salts especially K/Mg-double salt.

According to his present knowledge, the inventor is not aware of any single Mg-salts (as opposed to double salts) which are not hygroscopic. However, in case any single salts of magnesium which are not hygroscopic should turn out to exist, such single salts would of course be acceptable in the inventive salt product provided their taste is acceptable.

The salt product according to the invention consists preferably of NaCl and K/Mg-double salt and KCl and from 0 to 2% by weight of trace elements.

A salt product which in practice has proved to be suitable with respect to homogeneity and a good salt taste is characterised by comprising 15 to 70% by weight of NaCl, 1 to 85% by weight of K/Mg-double salt, the balance being KCl and/or trace elements.

In order to obtain a wholesome product, 0.7 to 1.3% by weight, preferably 0.9 to 1.1% by weight, such as about 1% by weight of trace elements can advantageously be present in each particle.

The invention also relates to a method for the preparation of a salt product comprising NaCl, K/Mg-double salt and optionally KCl, wherein the molar ratio of K to Mg is $\geq 1$, and wherein each of the salts is homogeneously distributed throughout the particles, which method is characterised by providing an aqueous salt mixture of the desired proportion of salt ions having a water content of 50 to 90% by weight and subjecting the aqueous salt mixture to a one-step instant drying at a temperature of 70° to 200° C. within a period of 1 to 60 seconds to obtain a dry product.

The aqueous salt mixture may be a slurry or a solution, preferably a solution.

According to a preferred embodiment, the instant drying is carried out by spray drying.

According to another preferred embodiment of the invention, the instant drying is carried out on the outer surface of a drum drier.

To ensure the instant drying on the drum drier, the outer surface thereof should have a temperature of 100 to 200° C., preferably 120° to 170° C. and most preferred 130 to 165° C.

When using a drum drier, the instant drying is preferably carried out by using a total contact time for the aqueous salt mixture and the obtained dried layer with the outer surface of the drum drier, i.e. from feeding the aqueous salt mixture onto the drum to the removal of the dried product, of from 1 to 60 seconds, preferably 6 to 40 seconds and most preferred 10 to 20 seconds, such as 12 to 16 seconds.

According to a preferred embodiment of the invention, the aqueous salt mixture is provided from a first portion containing potassium chloride and a second portion having a relative composition of salts similar to that of ocean water, apart from a reduced content of sodium chloride and optionally also of calcium salts.

As a suitable first portion can be used a portion derived from the so-called geobrine which with respect to its composition corresponds to ocean water apart from a reduced content of magnesium salts. Furthermore, the major amount of calcium is present as the chloride instead of the sulphate.

The further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

DETAILED DESCRIPTION OF THE INVENTION

The salt product according to the invention is prepared by providing an aqueous salt mixture in the form of a slurry or preferably a solution having the desired composition of ions, and drying this aqueous salt mixture instantly at a temperature of 70° to 200° C. in a period of time from 1 to 60 seconds.

There are several methods by which an aqueous salt mixture can be obtained from which the salt composition according to the present invention can be prepared. Thus, the aqueous salt mixture may be made from one or more portions derived from different sources.

For example, different ingredients from which the product can be made up can be added to pure water. For example magnesium, potassium and sodium salts such as magnesium sulphate, potassium chloride, sodium chloride and sodium sulphate can be dissolved in a sufficient amount of water to obtain an aqueous salt mixture in the form of a slurry or preferably a solution of these elements, and then drying the aqueous salt mixture at a temperature of 100° to 200° C. for a period of time of 1 to 60 seconds, after which the remaining product has a moisture content (excluding the water of crystallization of the double salts present) below 10%.

Additionally, potassium chloride or another soluble potassium salt, dissolved, as a saturated slurry or in the form of a dry powder, might be added as the first portion to a second portion of brine obtained from ocean or other sea water. Of course, the brine might contain a large amount of water, but such is not preferred since this extra amount of water needs to be evaporated. After all of the potassium has been dissolved in it, the aqueous salt mixture is dried in the manner described above.

As a suitable alternative, a crystal mixture of soluble sodium and potassium salts, dry or in the form of a slurry or as a solution, might be added as the first portion to a second portion of brine from which a part of or all sodium has been removed (e.g. bittern, which is a waste product of NaCl sea salt production).

According to the inventive method, the aqueous salt mixture can be either in the form of a slurry, or in the form of a solution. The latter is preferred, since the use of it provides a product which is more homogeneous. In other cases, the aqueous salt mixture is a saturated slurry containing only a small amount of non-dissolved crystals, which may act as grafting material.

A very suitable production method is obtained by use of a geobrine portion which comprises potassium chloride and sodium chloride. Such a geobrine is found, for example, in the Reykjanes area on Iceland in the form a geothermal brine. It can be characterised as ocean water which has penetrated the ground, whereby it has been almost completely freed of magnesium salts. Furthermore, the content of calcium sulphate has been replaced by calcium chloride. Such a brine comprises about 1 to 10% by weight NaCl, 0.01 to 5% by weight KCl and 0.1 to 5% by weight $CaCl_2$, preferably 1.5 to 5% by weight NaCl, 0.01 to 1% by weight KCl and 0.1 to 1.5% by weight $CaCl_2$. The geothermal brine is obtained together with steam, which can be used as a source of heat for the evaporation and/or the drying. Temperatures of the brine used can be in the range of 150° to 220° C.

The geothermal brine obtained at Reykjanes is a sterile brine without any content of toxic components and organic matters.

To obtain a process which is useful in practice, the water content of the aqueous salt mixture prior to drying should be at least 50% by weight, but not more than 90% by weight, preferably at least 60 but not more than 80% by weight of water, depending on the desired composition of the product and the temperature of the aqueous salt mixture.

Drum drying is preferred as a very suitable drying method. The temperature of the surface of the drum drier should be between 100° C. and 200° C., whereas the surface of the product on the drum drier usually shows a temperature between 120° and 170° C.

It is important that the drying takes place in one step without any fractioning since this would give an inhomogeneous distribution of the salts in the individual particles.

The salt products according to the invention can have a content of sodium chloride of at least 15% by weight, preferably at least 21% by weight, more preferred at least 25% by weight, and most preferred at least 30% by weight, and not more than 70% by weight, preferably not more than 65% by weight, more preferred not more than 52% by weight, and most preferred not more than 48% by weight.

The K/Mg-double salt can be selected among any double salts containing both potassium and magnesium. The most important K/Mg-double salts are carnallite and kainite.

Carnallite has the formula $KMgCl_3.6H_2O$. Kainite has the formula $KMgClSO_4.XH_2O$, where X is about 3. There is some discussion about the content of crystallization water in kainite. Some people skilled in the art say X=2.75, whereas others manintain that X=3.0.

Usually the content of K/Mg-double salt, calculated as carnallite in the inventive salt product is at least 1% by weight, preferably at least 5% by weight, more preferred at least 11% by weight, and most preferred at least 16% by weight, and not more than 85% by weight, preferably not more than 50% by weight, more preferred not more than 35% by weight, and most preferred not more than 24% by weight.

The amount of free potassium chloride, i.e. the additional amount of potassium chloride, which is not part of a double salt, can be 0% by weight, preferably at least 16% by weight, more preferred at least 26% by weight, and most preferred at least 29% by weight, and not more than 65% by weight, preferably not more than 48% by weight, more preferred not more than 38% by weight, and most preferred not more than 35% by weight.

The remaining components in the salt product, e.g. trace compounds and/or remaining amounts of calcium salts, usually amounts to from 0 to 2% by weight, for example about 1% by weight.

When potassium chloride is only present in the bound form in a double salt, the molar ratio of potassium to magnesium will be about 1:1 because the K:Mg ratio in the two major K/Mg-double salts carnallite and kainite in both cases is 1:1. If further free potassium chloride is present the molar ratio is greater than 1. The molar ratio of K to Mg in the inventive salt product will thus be at least 1:1, preferably at least 3:1, and more preferred 5:1, and not more than 20:1, preferably not more than 15:1, and most preferred not more than 13:1.

According to a preferred embodiment of the invention, the first portion is derived from geobrine, which is at first evaporated in order to precipitate a suitable amount of NaCl. The mother liquid is evaporated in order to crystallize NaCl+KCl and the remaning mother liquid, which contains calcium salts and siliceous compounds, is discharged. The obtained crystal mix of NaCl+KCl, which optionally comprises some water, is then mixed with the second portion in the form of a concentrated brine derived from ocean water and with a reduced content of NaCl and calcium salts. If necessary, water sufficient to obtain a water content of about 50 to 75% by weight is added to the mixture and the obtained solution is then dried instantaneously in the above mentioned manner, preferably on a drum drier. The product is obtained in the form of dry flakes which can be granulated and/or ground to the desired particle size. The composition of this product is normally 30 to 48% by weight of NaCl, 16 to 24% by weight of the double salts, about 1% by weight of trace elements and the balance being KCl.

The use of instant drying such as drum drying ensures that each particle is made up of an agglomerate of the salt crystals. This means that even the smallest particle, for instance resulting from crushing, has approximately the same composition as the entire salt product. In this way, no segregation can occur.

In practice, drum drying is performed using one or more rotating drum(s) having a heated outer surface. The drum can be heated in any conventional way, such as electrically or using a heat transfer medium. A preferred heat transfer medium is steam. As stated above, the outer surface temperature should be about 100° to 200° C.

The aqueous salt mixture to be dried can be fed to the drum in any conventional way. One way is by spraying. Another way is by using one or more applicator rolls. According to a preferred embodiment, use is made of a double drum system with two drums having opposite rotational directions. These two drums are situated with a narrow gap between them. The aqueous salt mixture is fed from a position above this narrow gap and a sump of warm aqueous salt mixture may be kept over the gap.

The dried salt, in the form of flakes, may be scraped from the drum with a conventional knife.

The angular distance between the feed position and the knife is normally between 60° and 300°, preferably between 120° and 270°.

To ensure the desired period of contact with the drum surface, the drum may have a speed of rotation from 0.2 to 10, preferably 0.5 to 5 r.p.m.

Thus, with an angular distance of 67.5° and a speed of 10 r.p.m., the contact period will be 1 second. With an angular distance of 180° and 0.5 r.p.m. the contact period is 60 seconds.

It will be appreciated that the drying period is not identical with the contact period. Thus, the major removal of water will take place during the first part of the contact period with no or only a minor amount of water being removed during the remaining part of the period.

This fact can be utilized in another embodiment, where feeding is provided by means of two or several applicator rolls. In this embodiment, a first amount of the aqueous salt mixture is fed by the first roll. When, after a short period the water has been removed, a second amount of aqueous salt mixture is fed by the second roll etc.

It is an advantage of the inventive product that it dissolves about 4 times as fast as commonly produced pure NaCl and that its bulk density is about 30% lower.

Moreover, in most cases it is not necessary to add anti-caking agents, as the salt product does not contain any hygroscopic Mg-salts.

Although the hygroscopic Mg-salts are avoided, the product normally has a substantial content of magnesium, which besides potassium, is considered important for the human health.

All the advantages as stated in the present specification may be obtained without the addition of any other component not commonly present in ocean water. Of course, additives might be added for other reasons, such as for the production of a seasoning salt composition.

The inventive product is a very pure, tasty and healthy product which is also stable and very applicable as a food additive (for preservation purposes), in the preparation of food (such as soups, butter, cheese, meat and beverages), as a table salt, and as a non-food additive (such as additives to pharmaceutical products).

EXAMPLE 1

Figure 1:
FIG. 1 shows a microphoto of the salt product obtained in Example 1.

Bittern is obtained from ocean water which is an aqueous salt mixture containing:

| NaCl | 2.6% by weight |
| KCl | 0.08% by weight |
| $MgCl_2$ | 0.3% by weight |
| $MgSO_4$ | 0.16% by weight |
| $CaSO_4$ | 0.16% by weight |
| NaBr | 0.008% by weight |
| $SiO_2$ | 0.001% by weight |

The ocean water is concentrated in an open basin provided with steam tubes. The preconcentrated ocean water is further concentrated in grainer pans also provided with steam tubes, precipitating part of the NaCl and gypsum. The salt crystals are removed from the grainer pans and discharged, leaving a mother liquor which comprises approximately 4.5% by weight $MgSO_4$, 6.7% by weight $MgCl_2$, 15.5% by weight NaCl and 1.5% by weight KCl and about 1% by weight of trace elements. This mother liquor is the normal by-product obtained by normal salt (NaCl) preparation and is termed bittern.

At Reykjanes, Iceland, a geothermal brine having the following characteristics is used:

Aqueous salt mixture containing:

| NaCl | 3.20% by weight |
| KCl | 0.37% by weight |
| $CaCl_2$ | 0.56% by weight |
| $CaSO_4$ | 0.003% by weight |
| $SiO_2$ | 0.08% by weight |
| Density | 0.91 kg/m$^3$ |
| Temperature | 180° C. |
| Absolute pressure af ground level: 1 MPa (10 bar) | |

This geothermal brine is concentrated in an evaporator until a concentration of about 7 to 8% by weight of the total salt was obtained. The heaters are heated with geothermal steam. The process condition in the crystallizer has been selected in such a way that KCl will remain in the solution. The precipitated NaCl is removed. The remaining mother liquor which contains about 9% by weight NaCl, 11.1% by weight KCl and 16.4% by weight $CaCl_2$ is then sent to a KCl/NaCl crystallization section. The liquor is concentrated to a $CaCl_2$ concentration of about 36% by weight in an evaporating crystallizer which operates at a temperature of about 40° C. A mixture of KCl/NaCl crystallizes. The crystal slurry so obtained is cooled down to 20° C. in a second stage crystallizer to crystallize more KCl. On a centrifuge, the mother liquor, mainly containing $CaCl_2$, is separated from the crystals and the crystals are washed. The mother liquor is discharged.

The KCl/NaCl crystal mixture is mixed with the above obtained bittern and some hot water and dissolved in such a way that a certain amount of the NaCl crystals does not dissolve. These crystals are removed. The obtained solution having a water content of about 75% by weight is then dried on a double drum drier having an outer surface temperature of about 140°–150° C. and a speed of rotation of 2.5 r.p.m. The angular distance between the feeding sump and the knife is approximately 210°, giving a contact period of about 14 seconds. The dried salt composition is scraped off from the drum in the form of dry flakes which may be granulated and/or ground to the desired particle size.

According to an analysis the product has the following composition:

| Chloride | 49.9% by weight |
| Sodium | 16.9% by weight |
| Magnesium | 2.0% by weight |
| Sulphate | 2.0% by weight |
| Calcium | 0.4% by weight |
| Potassium | 20.1% by weight |
| Borine | 0.007% by weight |
| Phosphate | 0.06% by weight |
| Selenium | 0.006% by weight |
| Tin | 0.002% by weight |
| Zinc | 0.001% by weight |

On the basis of this analysis, the following composition can be calculated:

| NaCl | 43.1% by weight |
| KCl | 32.1% by weight |
| Carnallite | 20.4% by weight |
| Kainite | 2.5% by weight |
| Balance | 1.8% by weight |

The total content of potassium chloride, both as free potassium chloride and bound in the double salts, is 38.4% by weight.

The salt product, Saga Salt 40, obtained has a good taste and according to preliminary tests it is an excellent substitute for ordinary salt both as regards taste, storability and technical effects.

Figure 2:
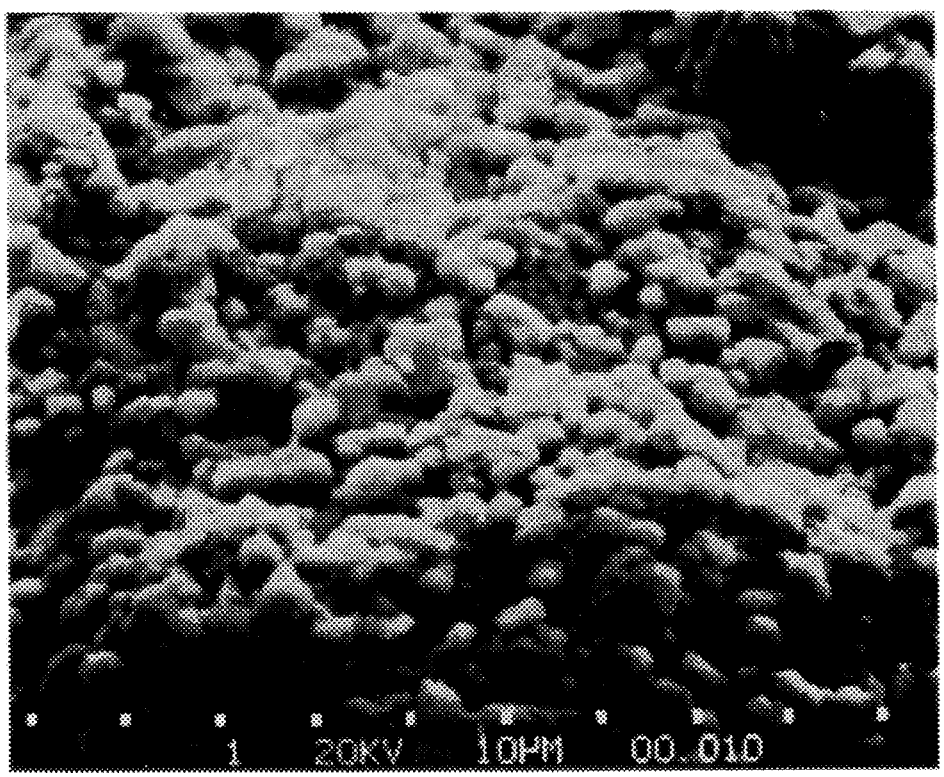
FIG. 2 is 30× enlargment of FIG. 1.
Figure 3:
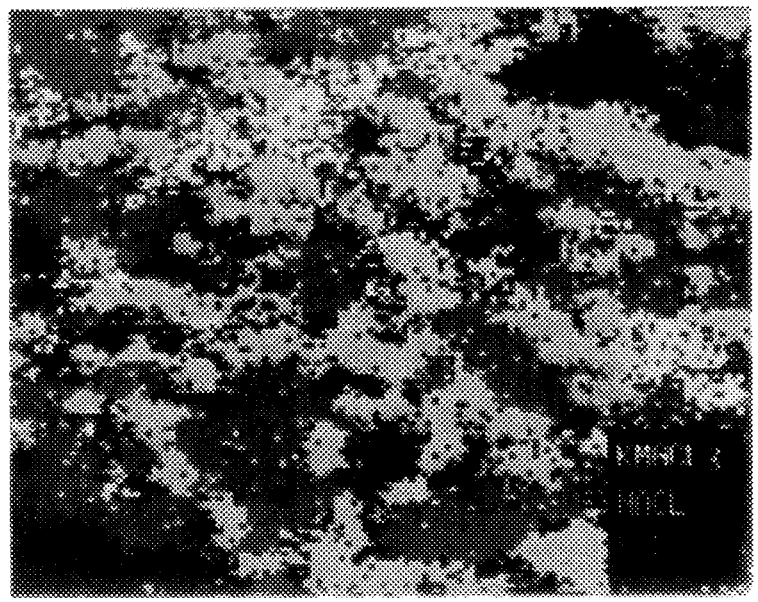
FIG. 3 is a computerized picture analysis of FIG. 2.

The salt product obtained is shown on the microphotos on FIGS. 1 and 2. The homogeneous distribution of KCl, NaCl and carnallite is demonstrated on the computerized picture analysis shown on FIG. 3.

EXAMPLE 2

A salt product having the following composition (Saga salt 50):

| NaCl | 54.8% by weight |
|---|---|
| KCl | 28.1% by weight |
| Carnallite | 14.3% by weight |
| Kainite | 1.8% by weight |
| Balance | 1.0% by weight | was prepared in the same way as in Example 1.

The composition was obtained by varying the proportions of the portions of bittern and the crystal mix derived from the geothermal brine, respectively, and the precipitation conditions.

The product has been tested at "Statens Mejeriforsøg" (The State Diary Trial Institute), Hillersd, Denmark, as a substitute for ordinary salt (NaCl) using Saga Salt 50 or NaCl in the same weight proportions in the preparation of butter, Danbo cheese 45+ and Danablue cheese 50+.

The result of these tests proved:

that the intensity of the taste when using Saga Salt 50 for the production of butter matches the intensity of taste of normally salted butter.

that the smell and the taste of butter salted with Saga Salt 50 and stored up to 8 weeks at 13° C., 5° C. and minus 18° C. do not deviate from those of normally salted butter.

the perioxide values and the acidity of butter salted with Saga Salt 50 and stored up to 8 weeks at 13° C., 5° C. and minus 18° C. do not deviate from those of corresponding butter produced with the use of normal salt.

that the smell and taste of Danbo cheese salted with brine made of Saga Salt 50 do not deviate from the smell and taste of normally salted Danbo cheese.

and that the smell and taste of Danablue cheese salted with Saga Salt 50 do not deviate from those of normally salted Danablue cheese after 8 weeks of curing.

EXAMPLE 3

Cooked cured ham was prepared using Saga Salt 50 in the same amount as ordinary salt. The salt level in that type of product is kept on 2.5 to 2.8% by weight. The addition of salt develops the cured meat flavour and enhances the retention of juiciness by increasing the water holding capacity. If the salt level is cut in such a product, this would result in losses of yield, shelf-life and quality. The replacement of the normal salt with Saga Salt 50 caused no noticeable changes in the taste or any other changes in the above mentioned function of salt addition.

EXAMPLE 4

Bacon is normally salted with 1.5 to 1.7% by weight of salt which ensures flavour, texture, colour and shelf-life. Reducing the salt level will have an negative influence on the above qualities. Replacing the normal salt with the same weight proportion of Saga Salt 50 did not cause any noticeable changes in the product.

EXAMPLE 5

Sausages of the emulsion-type are normally salted with 2.5% by weight of salt which provides colour, texture, emulsion stability and shelf-life. Furthermore, the salt prevents fat and water from oozeing out during the cooking by interacting with the salt soluble proteins. Flavour, texture, shelf-life and yield will be negatively influenced if the salt level is reduced. Replacing the normal salt with the same weight proportion of Saga Salt 50 causes no changes to the mentioned functionality.

EXAMPLE 6

Two parts by weight of bittern obtained as described in Example 1 and 8 parts by weight of a crystal mixture containing calculated as dry matter

| NaCl | 7.0% by weight |
|---|---|
| KCl | 92.5% by weight |
| $CaCl_2$ | 0.5% by weight | are mixed and further treated as described in Example 1. The obtained dry product has the following composition:

| NaCl | 15.4% by weight |
|---|---|
| KCl | 64.8% by weight |
| Kainite | 5.4% by weight |
| Carnallite | 13.7% by weight |
| Balance | 0.7% by weight |
| Molar ration K.Mg 13.:1 | |

EXAMPLE 7

Four parts by weight of bittern obtained as described in Example 1 are mixed with 6 parts by weight of a crystal mixture containing as dry matter

| NaCl | 82.5 by weight |
|---|---|
| KCl | 17.0% by weight |
| $CaCl_2$ | 0.5% by weight | and further treated as in Example 1. The dried product obtained has the following composition:

| NaCl | 62.6% by weight |
|---|---|
| KCl | 0.8% by weight |
| Kainite | 11.1% by weight |
| Carnallite | 24.7% by weight |
| Balance | 0.7% by weight |
| Molar ration K.Mg 1.22:1 | |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A method for the preparation of a salt product comprising NaCl, K/Mg-double salt and optionally KCl wherein the molar ratio of K to Mg is $\geq 1$, wherein the salt product comprises particles, in which NaCl, KCl, and K/Mg-double salt are homogeneously distributed throughout each particle, comprising providing an aqueous salt mixture of salt ions of NaCl, K/Mg double salt and optionally KCl, having a water content of 50 to 90% by weight and subjecting the aqueous salt mixture to a one-step instant drying at a temperature of 70° to 200° C. for a period of 1 to 60 seconds to obtain a dry product.

2. A method according to claim 1, wherein the aqueous salt mixture is in the form of a slurry or solution.

3. A method according to claim 1, wherein the aqueous salt mixture is subjected to instant drying by spray drying.

4. A method according to claim 1, wherein the aqueous salt mixture is subjected to instant drying on a drum drier.

5. A method according to claim 4, wherein the drum drier has an outer surface temperature of 100° to 200° C.

6. A method according to claim 4, wherein the aqueous salt mixture and the obtained dried layer are contacted with the outer surface of the drum drier for a period of from 1 to 60 seconds.

7. A method according to claim 1, wherein the aqueous salt mixture is prepared from a first portion containing potassium chloride and a second portion having a relative composition of salts as in ocean water, apart from a reduced content of sodium chloride, optionally also apart from a reduced content of calcium salts.

8. A method according to claim 7, wherein the first portion is derived from geobrine.

9. A method according to claim 1, wherein all ions of the salt component of said aqueous salt mixture are in solution form.

10. A method according to claim 4, wherein the drum dryer has an outer surface temperature of 120° to 170°.

11. A method according to claim 4, wherein the drum dryer has an outer surface temperature of 130° to 165° C.

12. A method according to claim 6, wherein said period is from 6 to 40 seconds.

13. A method according to claim 6, wherein said period is from 10 to 20 seconds.

* * * * *